US009002437B2

(12) United States Patent
Yaroshenko et al.

(10) Patent No.: US 9,002,437 B2
(45) Date of Patent: Apr. 7, 2015

(54) METHOD AND SYSTEM FOR POSITION ORIENTATION CORRECTION IN NAVIGATION (71) Applicant: General Electric Company, Schenectady, NY (US)

(72) Inventors: Andriy Yaroshenko, Garching (DE); Aghogho Obi, Troy, NY (US)

(73) Assignee: General Electric Company, Niskayuna, NY (US)

( * ) Notice: Subject to any disclaimer, the term of this patent is extended or adjusted under 35 U.S.C. 154(b) by 173 days.

(21) Appl. No.: 13/728,831

(22) Filed: Dec. 27, 2012

(65) Prior Publication Data
US 2014/0187915 A1     Jul. 3, 2014

(51) Int. Cl.
| A61B 5/06 | (2006.01) |
| A61B 6/12 | (2006.01) |
| A61B 1/313 | (2006.01) |
| A61B 17/06 | (2006.01) |

(Continued)

(52) U.S. Cl.
CPC .................. *A61B 5/062* (2013.01); *A61B 1/313* (2013.01); *A61B 17/06* (2013.01); *A61B 17/16* (2013.01); *A61B 17/28* (2013.01); *A61B 17/32* (2013.01); *A61B 17/34* (2013.01); *A61B 17/846* (2013.01); *A61B 17/86* (2013.01); *A61B 6/12* (2013.01); *A61B 6/54* (2013.01); *A61N 1/04* (2013.01); *A61B 19/5244* (2013.01); *A61B 6/032* (2013.01); *A61B 6/5247* (2013.01); *A61B 6/4441* (2013.01); *A61B 6/463* (2013.01); *A61B 6/487* (2013.01); *A61B 2019/5238* (2013.01); *A61B 2019/5251* (2013.01)

(58) Field of Classification Search
USPC ............. 600/411, 424, 427; 324/201, 207.15, 324/207.21; 702/150
See application file for complete search history.

(56) References Cited

U.S. PATENT DOCUMENTS

| 6,400,139 B1 | 6/2002 | Khalfin et al. |
| 7,911,202 B2 | 3/2011 | Anderson |

(Continued)

FOREIGN PATENT DOCUMENTS

WO     2011110966     9/2011

OTHER PUBLICATIONS

Kindratenko, Volodymyr V., "A survey of electromagnetic position tracker calibration techniques," Virtual Reality: Research, Development, and Applications, 2000, pp. 169-182, vol. 5, No. 3, University of Illinois at Urbana-Champaign, Urbana, IL, USA.

(Continued)

*Primary Examiner* — Michael Rozanski
(74) *Attorney, Agent, or Firm* — Robert M. McCarthy (57) ABSTRACT A method performed in a medical navigation system includes driving a transmitter at a first frequency and a second frequency to generate first and second electromagnetic fields, wherein the first and second frequencies are sufficiently low such that the first and second electromagnetic fields are frequency independent; receiving first and second distorted fields corresponding to the first and second electromagnetic fields, respectively, with each of at least two electromagnetic (EM) sensors attached to a surgical device; generating first and second signals in response to receiving the first and second distorted fields, respectively, using each of the at least two EM sensors; and determining a distortion in the first and second signals based at least on a distance between the at least two EM sensors and a difference between the first and second signals generated by each of the at least two EM sensors.

20 Claims, 7 Drawing Sheets (51) Int. Cl.

| | |
|---|---|
| *A61B 17/16* | (2006.01) |
| *A61B 17/28* | (2006.01) |
| *A61B 17/32* | (2006.01) |
| *A61B 17/34* | (2006.01) |
| *A61B 17/84* | (2006.01) |
| *A61B 17/86* | (2006.01) |
| *A61B 6/00* | (2006.01) |
| *A61N 1/04* | (2006.01) |
| *A61B 19/00* | (2006.01) |
| *A61B 6/03* | (2006.01) |

(56) References Cited

U.S. PATENT DOCUMENTS

| | | |
|---|---|---|
| 8,082,020 B2 | 12/2011 | Bar-Tal et al. |
| 2009/0082989 A1 | 3/2009 | Zuhars et al. |
| 2010/0127696 A1 | 5/2010 | Huber et al. |
| 2010/0168556 A1 | 7/2010 | Shen et al. |
| 2012/0323111 A1* | 12/2012 | Jain et al. ............ 600/411 |

OTHER PUBLICATIONS

Nafis, Christopher et al., "Method for estimating dynamic EM tracking accuracy of Surgical Navigation tools," Society of Photo-Optical Instrumentation Engineers, 2006, pp. 1-17, vol. 6141, SPIE Medical Imaging 2006 Proceedings, GE Global Research, GE Healthcare, Niskayuna, NY, USA.

Li, Mao et al., "A novel method of 6-DoF electromagnetic navigation system for surgical robot," Intelligent Control and Automation (WCICA), 2010, pp. 2163-2167, Shenzhen Institutes of Advanced Technology, Chinese Academy of Science, Shenzhen, China.

\* cited by examiner

METHOD AND SYSTEM FOR POSITION ORIENTATION CORRECTION IN NAVIGATION

BACKGROUND

In various medical contexts it may be desirable to acquire position and/or orientation information for a medical instrument, implant or device that is navigated or positioned (externally or internally) relative to a patient. For example, in surgical and/or interventional contexts, it may be useful to acquire position and/or orientation information for a medical device, or a portion of a medical device, when the device or relevant portion is otherwise out of view, such as within a patient's body. Likewise, in certain procedures where an imaging technique is used to observe all or part of the position and orientation information, it may be useful to have position and orientation information derived from the tracked device itself that can be related to the image data also being acquired.

Because some sensors operate based on electromagnetism, one issue that can arise with navigation sensors suitable for acquiring position and orientation information in this manner is the position and orientation errors that may be caused by the presence of metallic objects in the field of navigation. Unfortunately, these errors can result in incorrect positioning of a medical device during surgical or interventional procedures. Because of the relative ubiquity of metallic devices in such contexts, distortion is often unavoidable. Accordingly, it may be desirable to use systems that operate in an error free manner, even in environments that contain metallic objects. While, it may be desirable to use a navigation system that is able to compensate for distortions caused by metallic objects, in practice this may be difficult because the parameters of the metallic objects causing the distortion may be unpredictable.

BRIEF DESCRIPTION

In one embodiment, a method performed in a medical navigation system includes driving a transmitter at a first frequency and at least a second frequency to generate a first and a least a second electromagnetic field, wherein the first and second frequencies are sufficiently low such that the first and second electromagnetic fields are frequency independent; receiving a first and at least a second distorted field corresponding to the first and second electromagnetic fields, respectively, with each of at least two electromagnetic (EM) sensors attached to a surgical device; generating a first and at least a second signal in response to receiving the first and second distorted fields, respectively, using each of the at least two EM sensors; and determining a distortion in the first and at least the second signals based at least on a distance between the at least two EM sensors and a difference between the first and second signals generated by each of the at least two EM sensors.

In another embodiment, a medical navigation system includes a transmitter configured to emit electromagnetic (EM) fields in response to current at one or more frequencies; first and second EM sensors each configured to detect the EM fields emitted by the transmitter and to generate a signal representative of each detected EM field; and a computerized navigation system having one or more tangible, non-transitory, machine-readable media collectively storing instructions executable by a processor. The machine-readable media collectively storing instructions executable by a processor drives the transmitter at one or more frequencies to generate one or more EM fields, wherein the one or more frequencies are sufficiently low such that the one or more EM fields are frequency independent; measures one or more signals generated by the first EM sensor in response to detecting the one or more EM fields, respectively; measures one or more signals generated by the second EM sensor in response to detecting the one or more EM fields, respectively; and calculates a distortion in at least one of the one or more signals based at least on a distance between the first and second EM sensors, a change in the one or more signals, and the frequency response of the EM sensors when driven at a frequency of approximately zero.

Another embodiment includes one more tangible, non-transitory, machine-readable media collectively storing instructions executable by a processor. The machine-readable media collectively storing instructions executable by a processor drives the transmitter at one or more frequencies to generate one or more EM fields, wherein the one or more frequencies are sufficiently low such that the one or more EM fields are frequency independent; measures one or more signals generated by the first EM sensor in response to detecting the one or more EM fields, respectively; measures one or more signals generated by the second EM sensor in response to detecting the one or more EM fields, respectively; and calculates a distortion in at least one of the one or more signals based at least on a distance between the first and second EM sensors, a change in the one or more signals, and the frequency response of the EM sensors when driven at a frequency of approximately zero.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed herein, a navigation system may generally be attached to any one or a combination of a C-arm fluoroscope, an interventional device, and a patient, or may be suitable for use in a medical device, implant or instrument. The navigation system includes one or more electromagnetic (EM) sensors that transmit and/or receive information through the radiofrequency portions of the electromagnetic spectrum. The EM sensors may also be configured to produce a magnetic field that may be used to determine spatial properties, such as position coordinates and/or orientation information. However, the presence of conductive materials (e.g., metallic objects) within the magnetic field may distort spatial information related to the position and orientation of the EM sensors. The present disclosure is directed toward a navigation system with a position/orientation system that is suitable for correcting position and orientation errors due to field distortions caused by the presence of conductive materials in the field.

In certain embodiments, the position/orientation system uses characteristic behaviors of distorted fields in order to characterize the distortion of a given field arising from the presence of metallic objects. The characteristic behaviors of distorted fields may vary depending on the shape (e.g., spherical, irregular, and the like) of the metallic objects. In particular embodiments, the position/orientation system is configured to calculate field distortions caused by spherical metallic objects that are symmetrically shaped. In such an embodiment, the navigation system is driven at least two different frequencies, and the signal response emitted by the navigation system is detected. The position/orientation system uses the signal response to calculate the field distortion caused by the presence of the spherical metallic object within the field. The calculated field distortion is used to calculate the undistorted field (e.g., undistorted transmitter response), which is in turn used to determine the actual position and orientation of the medical device, implant or instrument attached to the navigation system.

In other embodiments, the position/orientation system is configured to calculate field distortions caused by metallic objects that are irregularly (e.g., non-spherical) shaped. In such embodiments, at least two sensors of the navigation system are driven at least at two different frequencies, and the signal responses emitted by the sensors are detected. The position/orientation system uses the signal responses from both sensors as well as other data (e.g., a known distance between the sensors) to calculate a field distortion caused by the presence of the irregularly shaped metallic object within the field. The calculated field distortion is used to calculate the undistorted field (e.g., undistorted transmitter response) at each sensor, and to determine the actual position and orientation of the medical device, implant or instrument attached to the sensors, after position and orientation error compensation.

In certain embodiments, a mathematical construct may be used to represent the signal response received from the sensors driven at various frequencies in terms of both the distorted field (e.g., distortion caused by metallic objects) and the undistorted field (e.g., the undistorted transmitter response). In such a construct, the actual signal received from the sensors may be represented by a sum of two terms, both consisting of two terms—an imaginary component and a real component. In accordance with the present disclosure the real component of the signal (e.g. field) represents the undistorted field while the distortion, in general, is represented by a term, consisting of both real and imaginary part of the signal (e.g. field). Such a mathematical construct may be employed to calculate, and then compensate for, the distortion caused by the metallic objects within and/or near the field of navigation.

Figure 1:
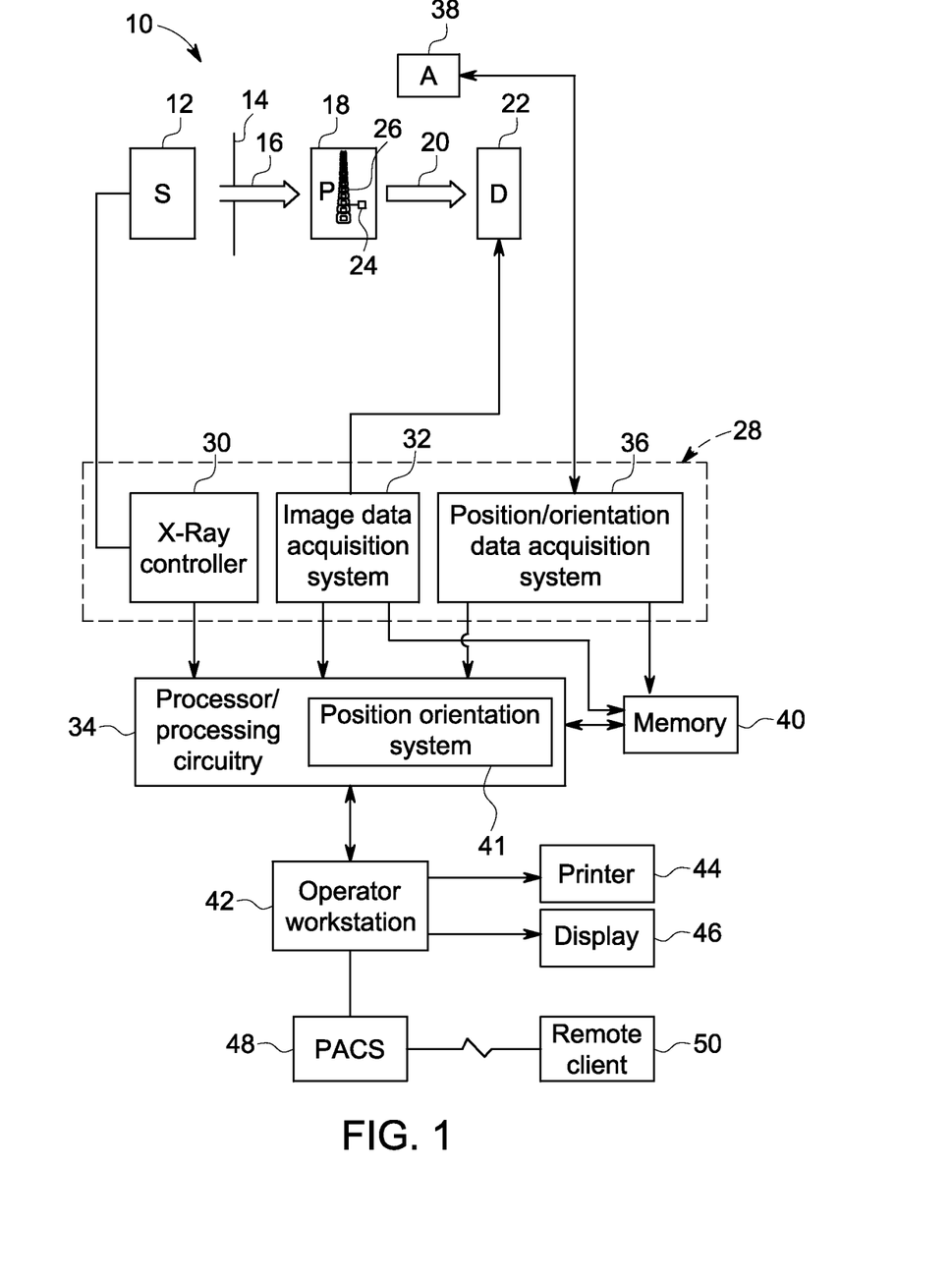
FIG. 1 is a block diagram depicting an embodiment of a fluoroscopy imaging system and a position determining system, in accordance with an embodiment of the present disclosure.

Moving now to the figures and referring initially to FIG. 1, a diagram of an X-ray based imaging system 10 for acquiring and registering fluoroscopic images and C-arm pose data is illustrated. In the illustrated embodiment, the imaging system 10 is a fluoroscopy imaging system designed to acquire two-dimensional X-ray projection data and, in some embodiments, to process the image for mapping and registration, and to correct for position and orientation errors in accordance with present embodiments. In the embodiment illustrated in FIG. 1, the X-ray based imaging system 10 includes a source of X-ray radiation 12 positioned adjacent to a collimator 14. The X-ray source 12 may be a standard X-ray tube or one or more solid-state X-ray emitters.

The collimator 14 permits a stream of radiation 16 to pass into a region in which a subject, such as a patient 18, is positioned. During operation, a portion of the radiation 20 passes through or around the patient 18 and impacts a detector array, represented generally as reference numeral 22. Detector elements of the array produce electrical signals that represent the intensity of the incident X-ray beam. In some embodiments, the signals generated by the detector array 22 may be subsequently processed to generate image or positional data that may be used in conjunction with data generated by an EM sensor 24 secured within the patient 18. For example, tracked images of an anatomy of interest (e.g., a vertebral column) 26 may be registered and visualized in the depicted embodiment.

The source 12 is controlled by a system controller 28, which furnishes both power and control signals for examination procedures. Moreover, the detector 22 is coupled to the system controller 28, which commands acquisition of the signals generated in the detector 22. In general, system controller 28 commands operation of the imaging system 10 to execute examination protocols and, in some embodiments, to process acquired data. In the present context, system controller 28 also includes signal processing circuitry, typically based upon a general purpose or application-specific digital computer, associated memory circuitry for storing programs and routines executed by the computer (such as programs and routines for implementing the present technique), as well as configuration parameters and image data, interface circuits, and so forth. Additionally, an X-ray controller 30 disposed within the system controller 28 may control the source 12 of radiation. Particularly, the X-ray controller 30 may be configured to provide power and timing signals to the X-ray source 12.

The system controller 28 is also illustrated as including an image data acquisition system 32. In this embodiment, the detector 22 is coupled to the system controller 28, and more particularly to the image data acquisition system 32. The image data acquisition system 32 receives data collected by readout electronics of the detector 22. In one embodiment, the image data acquisition system 32 receives sampled analog signals from the detector 22 and converts the data to digital signals for subsequent processing by processing circuitry 34, which may, for example, be one or more processors of a general or application specific computer.

In accordance with an embodiment, the system controller 28 also includes a position/orientation data acquisition system 36 configured to acquire position and orientation data from one or more antennas 38. During operation, the one or more antennas 38 detect signals and/or fields generated by some or all of the EM sensor elements 24, 54 and 56 (depicted in FIG. 2). That is, the position/orientation data acquisition system 36 processes signals acquired from the antennas 38 to generate position and/or orientation information about the EM sensor 24 (and thus the anatomy of interest 26) as well as other EM sensors in proximity to the imaging system 10. The position and/or orientation information generated by the position/orientation data acquisition system 36 may be provided to the processing circuitry 34 and/or a memory 40 for subsequent processing. It should be understood that the antenna 38 could either receive the signals/fields from the EM sensor elements or the antenna could generate the signals/field that are received by the EM sensor elements. Also, one of the EM sensor elements could take the place of the antenna.

The processing circuitry 34 is typically coupled to the system controller 28. The data collected by the image data acquisition system 32 and/or by the position/orientation data acquisition system 36 may be transmitted to the processing circuitry 34 for subsequent mapping of the EM sensor data to the fluoroscopic data, or for subsequent position and/or orientation errors caused by metallic objects within the field. In particular, the processing circuitry 34 may include a position/orientation system 41 for correcting position and orientation errors due to field distortions caused by the presence of spherical (i.e., symmetrical) or irregular (i.e., non-symmetrical) metallic objects. The position/orientation system 41 may apply characteristic behaviors of distorted fields to the measured data gathered by the position/orientation data acquisition system 36 in order to calculate the field distortion. The calculated field distortion may then be used to calculate the undistorted field (e.g., a field unaffected by metallic objects) and to obtain the actual position and orientation of the sensors 24, 54, and 56 (depicted in FIG. 2). The position/orientation system 41 sends the correct position and orientation of the sensors 24, 54, and 56 to the system controller 28, which may then alter operational commands of the imaging system 10 in order to compensate for the position and orientation errors. In other embodiments, corrected images may be displayed having corrected data.

The processing circuitry 34 may include (or may communicate with) the memory 40 that stores data processed by the processing circuitry 34 or data to be processed (such as fluoroscopic images produced by the imaging of patient 18 or position/orientation data) by the processing circuitry 34. It should be understood that any type of computer accessible memory device capable of storing the desired amount of data and/or code may be utilized by the imaging system 10. Moreover, the memory 40 may include one or more memory devices, such as magnetic, solid state, or optical devices, of similar or different types, which may be local and/or remote to the system 10. The memory 40 may store data, processing parameters, and/or computer programs having one or more routines for performing the processes described herein.

The processing circuitry 34 may be adapted to control features enabled by the system controller 28, e.g., scanning operations and position/orientation data acquisition. For example, the processing circuitry 34 may be configured to receive commands and scanning parameters from an operator via an operator interface 42 typically equipped with, for example, a keyboard, mouse and/or other input devices. An operator may thereby control the system 10 via the input devices. A display 46 coupled to the operator interface 42 may be utilized to observe a tracked and registered 2D or 3D scan having data corrected in accordance with the present disclosure. For example, the display 46 may be used to display the first position of the surgical device relative to the transmitter on a 2D or 3D representation of at least the patient and the surgical device. It may then update the displayed position of the surgical device based on the correct position and orientation information calculated by the position/orientation system 41. In certain embodiments, the 2D representation may be an X-Ray image, and the 3D representation may be of a CT image, a CT/MR image, or a combination thereof.

Additionally, an image may be printed by a printer 44, which may be coupled to the operator interface 42. In some embodiments, one or more operator interfaces 42 may be linked to the system 10 for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The processing circuitry 34 may also be coupled to a picture archiving and communications system (PACS) 48. Image data generated or processed by the processing circuitry 34 may be transmitted to and stored at the PACS 48 for subsequent processing or review. It should be noted that PACS 48 might be coupled to a remote client 50, radiology department information system (RIS), hospital information system (HIS) or to an internal or external network, so that others at different locations may gain access to the image data.

Figure 2:
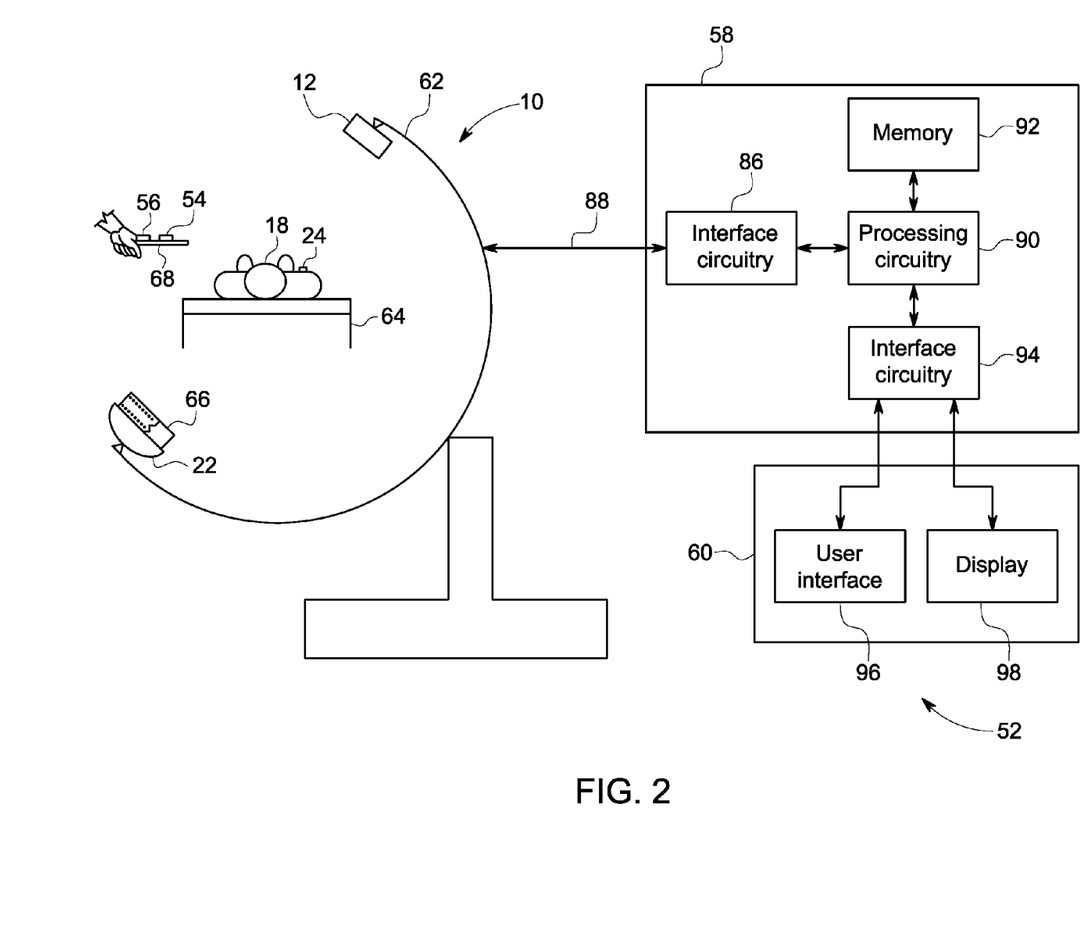
FIG. 2 is a schematic diagram of an embodiment of a surgical navigation system in accordance with an aspect of the present disclosure.

To discuss embodiments of the present technique in greater detail, a specific medical imaging modality based generally upon the overall system architecture outlined in FIG. 1 is depicted in FIG. 2, wherein a surgical navigation system 52 is illustrated. It may be appreciated that the system 52 may contain features included in system 10 illustrated in FIG. 1. As such, those features are described using the same numerical reference. In the illustrated embodiment, the navigation system 52 includes tracking components that include electromagnetic (EM) sensors 24, 54, and 56. The sensors 24, 54, and 56 may be magnetoresistance-based sensors, or electromagnetic coil-based sensors. Further, the surgical navigation system 52 includes an embodiment of the X-ray imaging system 10 for acquiring and, in some embodiments, processing image data. As illustrated in this embodiment, surgical navigation system 52 further includes a computerized navigation system 58 and workstation 60.

The X-ray imaging system 10 is illustrated as a C-arm fluoroscopy system that includes a C-arm 62, X-ray radiation source 12, and X-ray detector 22. The X-ray radiation source 12 is mounted on the C-arm 62, and the X-ray detector 22 is mounted on the C-arm 62 in an opposing location from the X-ray radiation source 12. While in some radiographic systems the X-ray radiation source 12 and the X-ray detector 22 may be fixed, in some fluoroscopy system the C-arm 62 allows for coordinated movement of the X-ray radiation source 12 and the X-ray detector 22 about the patient 18. The X-ray detector 22 receives a portion the stream of radiation 20 from the X-ray source 12 that passes through the patient 18 positioned on a table 64. The X-ray detector 22 produces electrical signals that represent the intensity of the radiation stream. These signals are suitably acquired and processed to track and subsequently image features within the subject.

A plurality of EM sensors may be fixed in relation to the fluoroscopy system. In the illustrated embodiment, the EM sensor 24 is fixed on the patient 18, though it should be noted that EM sensor 24 may be fixed within the patient 18, for example, to an internal structure of interest, such as a skeletal feature. EM sensors 54 and 56, on the other hand, move in relation to the system 10. In particular, the EM sensors 54 and 56 may be fixed in relation to a medical (e.g., surgical) device 68. In the illustrated embodiment, the EM sensors 54 and 56 are mounted on the operative end of the medical device 68. Device 68 may be may be any suitable device for use in a medical procedure. For example, device 68 may be a pointer, a drill, a guide wire, a catheter, an endoscope, a laparoscope, a biopsy needle, an ablation device or other similar devices. Thus, the surgical device 68 may include one or more metallic materials that cause distortions in the field detected by the position/orientation system 41.

In a general sense, the EM sensors 24, 54 and 56 may be implemented as non-optical EM receivers or non-optical EM transmitters, i.e., as EM components that transmit and/or receive using portions of the EM spectrum that do not correspond to optical or visible light. For example, in some applications of the present technique, the EM sensors 24, 54 and 56 may employ the radiofrequency (RF) portion of the electromagnetic spectrum and have a working range of between about 3 inches to about 18 inches. While any one or a combination of the EM sensors 24, 54 and 56 may be used as transmitting or receiving coils, in one embodiment, the EM sensor 24 may be implemented as an EM transmitter, while the remaining EM sensors 54 and 56 may be implemented as EM receivers. In such an embodiment, the signals sensed by EM sensors 54 and 56 that are fixed in relation to the device 68 may be used to determine the spatial properties of the device 68, for example, the position (e.g., the X-, Y-, and Z-coordinates) and orientation (e.g., the pitch, yaw, and roll angles). As will be appreciated, the mutual inductance of two EM sensors is the same, regardless as to which is the receiver and the transmitter. Therefore, relative positioning and functionality of the EM receivers and transmitters may be reversed. For example, the EM sensor 24 that is fixed in relation to the patient may be implemented as an EM receiver, while the remaining EM sensors 54 and 56 may be implemented as EM transmitters. Likewise, any other suitable combination of EM transmitters and receivers may be implemented as the EM sensors 24, 54, and 56.

In some embodiments, each of the EM sensors 24, 54 and 56 may contain materials (e.g., coils, current loops, electromagnets, etc.) capable of producing a dipole magnetic field when a current is applied to or induced through them. Electromagnetic fields generated by each of the dipoles are distinguishable from one another in phase, frequency, time division multiplexing, and the like. The near-field characteristics of the electromagnetic fields may be used to determine spatial properties, such as position coordinates and/or orientation information. In some embodiments, one or more of the EM sensors 24, 54 and 56 may employ industry-standard coil architecture (ISCA) type coils, a single dipole coil, or a combination thereof. ISCA coils generally may be defined as three, approximately collocated, approximately orthogonal, and approximately dipole coils. Alternatively, one or more of the EM sensors 24, 54 and 56 may be configured with a single coil that generates a single dipole magnetic field. In addition, one or more of the EM sensors 24, 54 and 56 may employ technologies other than a coil, including, for example, Hall Effect, magnetoresistance, or flux gate devices. In certain embodiments, the EM sensors 24, 54 and 56 may operate in a wired or wireless configuration.

In some embodiments, during operation of the surgical navigation system 52, the electromagnetic field generated by each of the EM sensors 24, 54, and 56 may become distorted by conductive materials near the field. Conductive materials that interfere with the electromagnetic field may include spherical or irregular metallic objects, such as, for example, the metal of the C-arm 62, the surgical tool to which the EM sensors 54 and 56 are attached, metal implants within the patient 18, or the like. Metallic objects may cause two metal-related occurrences that distort the electromagnetic field and cause position and orientation errors in the navigation system 52. For example, in one occurrence, non-magnetic metallic objects may introduce field distortions due to eddy currents, which are induced by metals in a time varying magnetic field. Eddy currents typically produce significant distortion fields when the EM sensors 24, 54, and 56 of the navigation system 52 are driven at frequencies approximately higher than 500 Hz. By further example, in another occurrence, ferromagnetic objects (e.g., magnetic metallic objects) lead to significant distortions in the generated field due to magnetization. The field generated by the EM sensor responds to ferromagnetic objects in a characteristic manner (certain relation between real and imaginary parts of the induced distortion field) at low frequencies, and thus, may be used as a characteristic behavior when determining the position and orientation errors of the navigation system 52. As discussed below, with respect to FIGS. 3-5, the present disclosure provides embodiments of methods for the reduction of these types of distortions.

As noted above, the surgical navigation system 52 may further include the computerized navigation system 58. In the illustrated embodiment, the computerized navigation system 58 includes interface circuitry 86 for receiving tracking and imaging data, represented generally by arrow 88. In some embodiments, some or all of the tracking and imaging data 88 that is sent to the computerized navigation system 58 has been processed and analyzed by the processing circuitry 34 and memory 48 of imaging system 10. The computerized navigation system 58 may also include processing circuitry 90, memory unit 92, and workstation interface circuitry 94. As will be appreciated, one or more computers may be used to implement the computerized navigation system 58. In general, the processing circuitry 90, which may include a digital signal processor, a CPU or the like, may process the tracking data so that the location of the device 68 may be tracked, mapped and registered to a pre-operative 3D scan. Memory unit 92 may serve to save the imaging and tracking data as well as other system parameters. In some embodiments, the memory unit 92 may be any computer-readable medium such as an optical media (e.g., compact discs, digital video discs), a solid-state memory device (USB drive, flash drive), a hard drive, a memory card, and the like. In one embodiment, the memory unit 92 contains computer code that is executed by the processing circuitry 90. The workstation interface circuitry 94 may be configured for communicating with workstation 68.

As illustrated, the surgical navigation system 52 further includes the workstation 68, which includes a user interface 96 and a display 98, which may or may not correspond to operator interface 42 and display 44 depicted in FIG. 1. The user interface 96 may include a keyboard and/or mouse, as well as other devices such as printers or other peripherals for reproducing hardcopies of the reconstructed images. Display 98 may include one or more screens. For example, the display 98 may include a first screen for displaying a previously acquired image and a second screen for displaying one or more intra-operative images.

Figure 3:
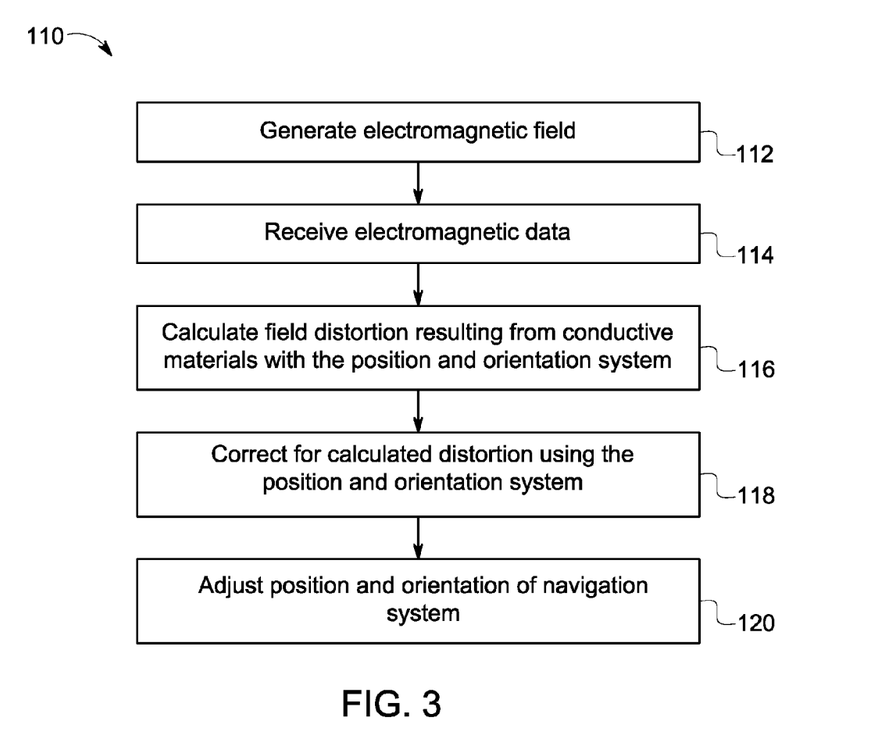
FIG. 3 is a flowchart depicting an embodiment of a method for adjusting the position and orientation of a device based on calculated field distortions in accordance with an aspect of the present disclosure.

FIG. 3 is a flowchart depicting an embodiment of a method 110 for adjusting the position and orientation of a device 68 based on calculated field distortions. As depicted in block 112, an electromagnetic field is generated by the navigation system 52 (shown in FIG. 2), such as by an EM sensor in a transmitting mode and which may be generally be attached to each of a C-arm fluoroscope, an interventional device, and a patient, or may be suitable for use in a medical device, implant or instrument. Again, as previously described with respect to FIG. 2, each of the EM sensors 24, 54 and 56 in the navigation system 52 may be capable of producing an electromagnetic field when a suitable current is applied to or induced through them. In accordance with present embodiments, the current is varied at a rate below 1 kHz, such as below 750 Hz or 500 Hz. Furthermore, each of the EM sensors 24, 54, and 56 of the navigation system 52 may employ the radiofrequency (RF) portion of the electromagnetic spectrum, and may be implemented as either EM transmitters or EM receivers. For example, in one embodiment of block 112, EM sensor 24 may be implemented as an EM transmitter, while the remaining EM sensors 54 and 56 may be implemented as EM receivers. In this embodiment, the signals transmitted by EM sensor 24 may be received by EM sensors 54 and 56 as electromagnetic data (block 114).

In particular, the electromagnetic field generated by the EM sensor 24 may induce a current in the EM sensors 54 and 56, which is in turn relayed as data to the surgical navigation system 52. The electromagnetic data received by EM sensors 54 and 56 that are fixed in relation to the device 68 may be used to determine the spatial properties of the device 68, for example, the position (e.g., the X-, Y-, and Z-coordinates) and orientation (e.g., the pitch, yaw, and roll angles). Again, the presence of conductive materials within the field, such as spherically or irregularly shaped metallic objects, may cause spatial distortions of the field generated by the EM sensor 24, and thus, the position and orientation of the device 68 (as indicated by the signals generated at the EM sensors 54 and 56) may be distorted. In other words, if distorted electromagnetic data is received by EM sensors 54 and 56 (or other receiving array), then the position (e.g., the X-, Y-, and Z-coordinates) and orientation (e.g., the pitch, yaw, and roll angles) data generated may also be distorted.

As depicted in block 116, the position/orientation system 41 (FIG. 1), may be used to calculate field distortions caused by conductive materials within and/or near the field. In certain embodiments, the position/orientation system 41 uses characteristic behaviors of distorted fields in order to calculate field distortions caused by metallic objects to avoid or correct for position and orientation errors. The characteristic behaviors of distorted fields for non-magnetic metallic objects and ferromagnetic objects (e.g., magnetic metallic objects) are generally different. For example, eddy currents, which are induced by non-magnetic metallic objects in a changing magnetic field, are generally seen when the navigation system 52 is driven at frequencies approximately higher than 500 Hz. In order to avoid, or correct for, field distortions caused by eddy currents, the navigation system 52 is driven at frequencies lower than approximately 1 kHz, such as below approximately, or between approximately 100 and 500 Hz. Furthermore, ferromagnetic objects (e.g., magnetic metallic objects) that cause field distortions even at frequencies lower than approximately 500 Hz also exhibit characteristic behaviors. For example, the field emitted by the transmitting EM sensor (e.g., EM sensor 24), for frequencies lower than 500 Hz, is frequency independent. In other words, when the transmitting EM sensor is driven at various frequencies below 500 Hz, the field generated by the EM sensor is independent of frequency and responds to the ferromagnetic material in an identical manner when a scale factor is applied.

In yet other embodiments, the position/orientation system 41 calculates field distortions caused by conductive materials based on the shape of the conductive materials. For example, conductive materials, such as metallic objects, may be spherically shaped (i.e., symmetrical) or irregularly shaped (i.e., non-symmetrical). In particular embodiments, the position/orientation system 41 is configured to calculate field distortions caused by spherical metallic objects that are symmetrically shaped. In such an embodiment, the navigation system 52 is driven at at least two different frequencies. Both frequencies are generally lower than approximately 500 Hz so that the change in response from one frequency to another can be attributed to the distortion. One or more receiving EM sensors (e.g., EM sensors 54 and 56) detect the signal responses emitted by the receiving EM sensors of the navigation system 52 at each of the frequencies. The position/orientation system 41 uses the signal responses to calculate the field distortion caused by the presence of the spherical metallic object within the field. In certain embodiments, characteristic behaviors of the distorted field for spherical metallic objects are used to calculate the field distortions, as further described below with respect to FIG. 4.

In yet other embodiments, discussed in detail below with respect to FIG. 5, the position/orientation system 41 is configured to calculate field distortions caused by metallic objects that are irregularly (e.g., non-spherical or only partially spherically) shaped. In such embodiments, the navigation system 52, having at least one transmitter (e.g., EM sensor 24) and at least two receiving EM sensors (e.g., EM sensors 54 and 56), is driven at least at two different frequencies. Both frequencies are generally lower than approximately 500 Hz so that characteristic behaviors of distorted fields may be used in determining the field distortion. The field emitted by the transmitter is detected by at least two receiving EM sensors, such as, for example, EM sensors 54 and 56. The position/orientation system 41 uses the signal responses from both sensors, the undistorted component of which is frequency independent, to calculate the field distortion caused by the presence of the irregularly shaped metallic objects within the field. In yet other embodiments, the position/orientation system 41 calculates field distortions caused by conductive materials based on the characteristic behaviors of distorted fields, the shape of the conductive materials, or a combination thereof.

The position/orientation system 41 corrects the actual position and orientation data based on the previously calculated field distortion, and thus compensates for the distortions caused by spherical or irregularly shaped conductive materials within and/or near the field (block 118). For example, the distortion calculated may be in the form of position (e.g., the X-, Y-, and Z-coordinates) and orientation (e.g., the pitch, yaw, and roll angles), as depicted in block 116. In correcting signals generated by the receiving EM sensors (e.g., EM sensors 54 and 56) to obtain the undistorted portion of the signal, the position and orientation errors contained within the received signals is also removed. Furthermore, once the actual position and orientation coordinates of the EM sensors 24, 54, and 56 are determined, the position and orientation of the medical device, implant, or instrument attached to the sensors of the navigation system 52 is adjusted to compensate for position and orientation errors caused by conductive materials.

Figure 4:
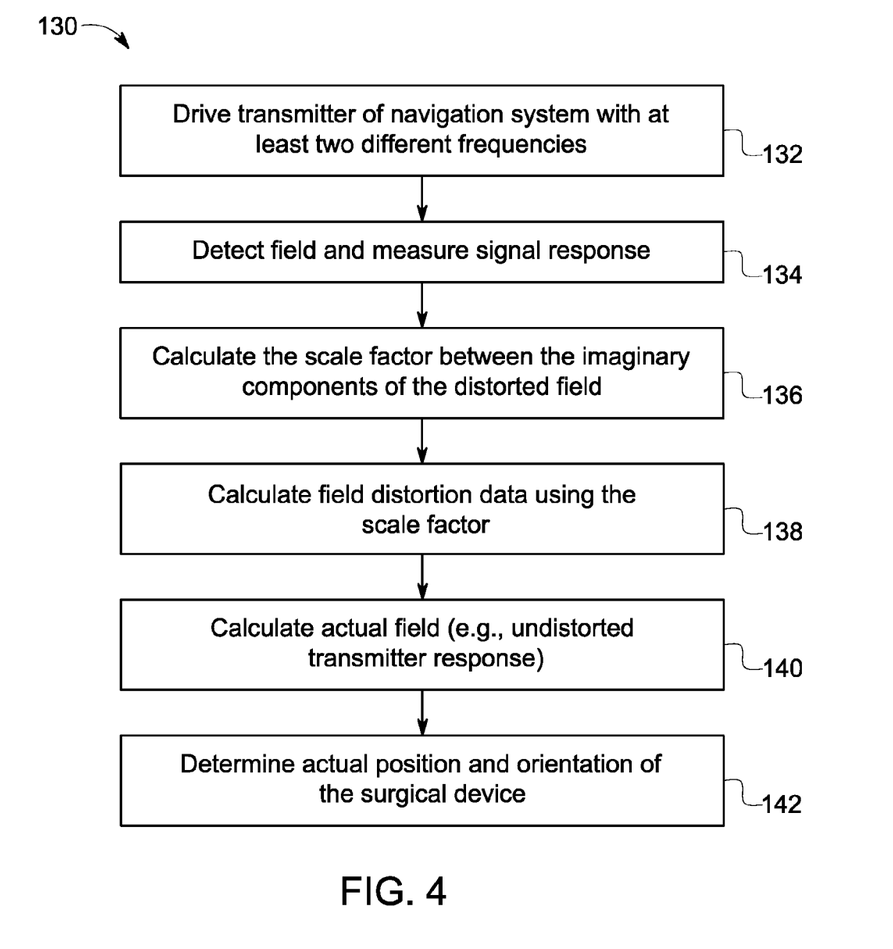
FIG. 4 is a flowchart depicting an embodiment of a method for calculating field distortions caused by spherical metallic objects that are symmetrically shaped in accordance with an aspect of the present disclosure.

FIG. 4 is a flowchart depicting an embodiment of a method 130 for calculating field distortions caused by spherical metallic objects. As depicted in block 132, the sensors of the navigation system 52 (e.g., EM sensor 24) is driven at at least two different frequencies. As described in FIG. 3 above, both frequencies are generally lower than approximately 1 kHz so that the signal variation between the two frequencies is attributable to distortion. The fields emitted at both frequencies by the EM sensor(s) of the navigation system 52 are detected and measured (block 134). For example, the EM sensors 54 and 56 may detect the field emitted by the EM sensor 24 at both frequencies, and may generate a signal therefrom (e.g., a signal response). These signals may subsequently be measured.

Mathematically, the signal responses of the EM sensors 54 and 56 may be considered to include, or, in one embodiment, to consist of a real component and an imaginary component. The real component of the mathematical representation of the signal response represents is created by two contributions: the undistorted transmitter response (e.g., a response to the undistorted field) and the real part of the distortion field. The imaginary component of mathematical representation of the signal response represents the only field distortion caused by conductive materials within the field (e.g., distorted field). The signal response is the hypothetical combination of the real component with the imaginary component, and represents the signal as it received by the EM sensors (e.g., EM sensors 54 and 56).

In certain embodiments, the characteristic behaviors of spherical ferromagnetic objects in magnetic fields, as described above, are used to calculate the field distortions they cause. For example, one such characteristic behavior of spherical ferromagnetic objects is that for frequencies lower than 500 Hz, the real component of the distortion field is very high for low frequencies and decreases in magnitude as the frequency increases. Furthermore, the imaginary component of the distortion field is small for low frequencies and increases with frequency up to a peak value before it decreases once again. In short, for spherically shaped ferromagnetic objects, there is a correlation between the real component and the imaginary component at frequencies lower than approximately 500 Hz. This correlation can be used to determine the imaginary component (e.g., distortion) of the signal response. Furthermore, as described in FIG. 3 above, at frequencies lower than 500 Hz, the field of the transmitter is frequency independent. In other words, when transmitting at various frequencies below 500 Hz, the field generated by the EM sensor is independent of frequency and responds to the spherical ferromagnetic object in an identical manner when a scale factor is applied. As depicted in block 136, the scale factor between the imaginary components of the signal responses at both frequencies is calculated. Given the scale factor between the imaginary components, and based on the known correlation between the real component and the imaginary component of the signal response in the presence of spherical ferromagnetic objects at low frequencies, the field distortion can be calculated (block 138). Ultimately, the field distortion can be removed to obtain corrected position and orientation information.

In one embodiment, the measured signal response of the receiving EM sensors of the navigation system 52, when distorted by a spherical metallic object at a first frequency below 500 Hz, can be described in equation (1) as:

$$M_1 = C_1 + X_1 \quad (1)$$

where $M_1$ is the signal response at the first frequency, $C_1$ is the real component of the undistorted response (e.g., undistorted transmitter response or undistorted field), and $X_1$ is the real and imaginary component of the signal response (e.g., distortion caused by the spherical conductive materials). Furthermore, the measured signal response of the receiving EM sensors of the navigation system 52, when distorted by a spherical metallic object at a second frequency below 500 Hz, can be described in equation (2) as:

$$M_2 = C_1 + (K * X_1) \quad (2)$$

where $M_2$ is the signal response of the navigation system 52 at the second frequency, $C_1$ is the real component of the undistorted response (e.g., undistorted transmitter response or undistorted field), $X_1$ is the real and imaginary component of the signal response (e.g., distortion caused by the spherical conductive materials), and K is the scale factor (e.g., ratio) between the imaginary and real components at the two different frequencies. In a graphical representation of the response, the scale factor may be considered to be the slope of the graph. As described in detail above, the signal response generated at different frequencies is independent of frequency when the navigation system 52 is driven at frequencies lower than approximately 500 Hz, and responds to the spherical ferromagnetic object in an identical manner when a scale factor is applied. Indeed, since the undistorted field consists only of a real component, the imaginary parts of the field are measured directly in $M_1$ and $M_2$ and the scaling factor K can be calculated. Thus, given the measured signal responses $M_1$ and $M_2$ and the calculated K scaled factor, the imaginary component and the real component can be calculated, and the field distortion can be determined.

As described in FIG. 3, the calculated field distortion data (block 138) is used by the position/orientation system 41 to calculate the actual field (e.g., undistorted transmitter response) (block 118). Furthermore, once the actual position and orientation coordinates of the EM sensors 24, 54, and 56 are determined, the position and orientation of the device 68, implant or instrument in communication with the navigation system 52 is adjusted to compensate for position and orientation errors (block 142).

Figure 5:
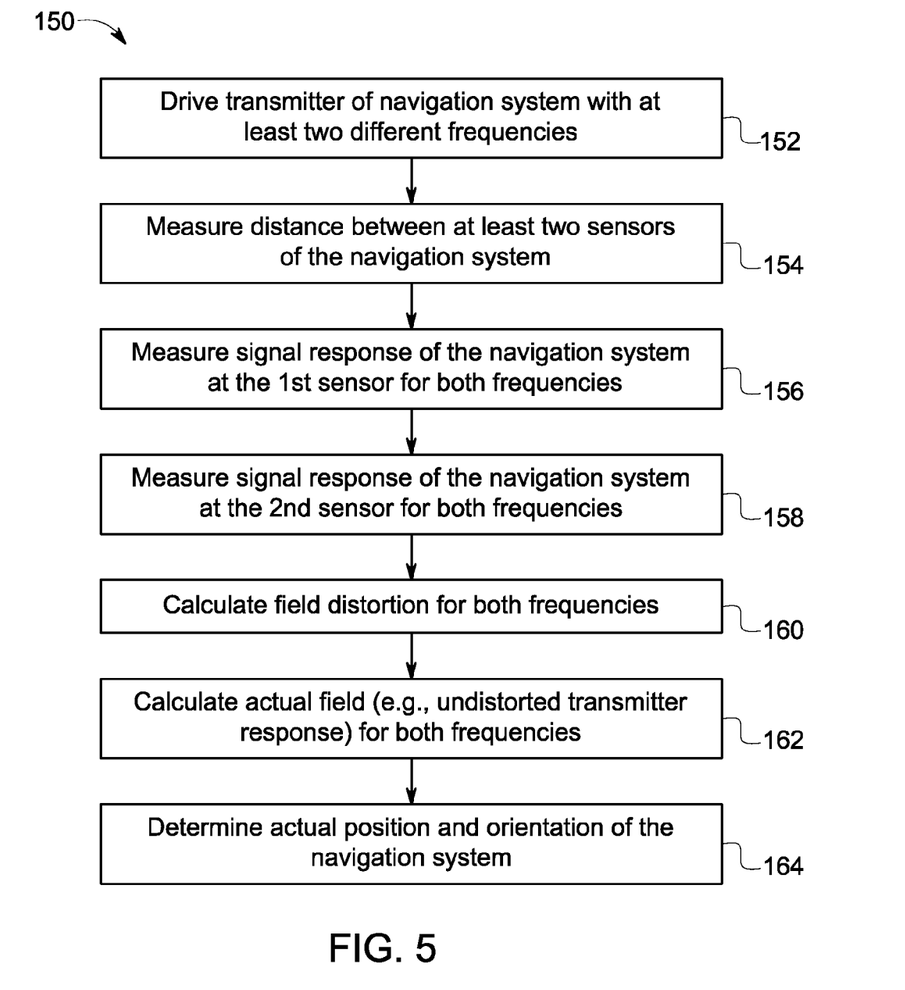
FIG. 5 is a flowchart depicting an embodiment of a method for calculating field distortions caused by non-spherical metallic objects in accordance with an aspect of the present disclosure.

FIG. 5 is a flowchart depicting an embodiment of a method 150 for calculating field distortions caused by metallic objects that are irregularly (e.g., non-spherically) shaped. Again, such objects may include for example, the metal of the C-arm 62, the surgical tool to which the EM sensors 54 and 56 are attached, metal implants within the patient 18, or the like. As depicted in block 152, the transmitter of the navigation system 52 (e.g., EM sensor 24) is driven at at least two different frequencies. As described in FIG. 3 above, both frequencies are generally lower than approximately 500 Hz so that the change in the field detected by receivers of the navigation system 52 is attributable to distortion.

In certain embodiments, at least two EM sensors may be used to receive the field emitted by the transmitter (e.g., EM sensor 24) of the navigation system 52. In particular, the at least two EM sensors (e.g., EM sensors 54 and 56) are used to calculate field distortions caused by metallic objects that are irregularly shaped. In accordance with present embodiments, the variables used to calculate the distortion include the frequencies used to drive the transmitter, the signal responses by the receiving EM sensors (which may vary due only to changes in distortion), and a distance between the receiving sensors, which is fixed. Accordingly, the method 150 includes measuring (block 154) a distance between at least two receiving sensors of the navigation system 52. It should be noted that the distance may be measured at any suitable time, and not necessarily after the generation of the field by the transmitter of the navigation system 52 as depicted in the illustrated embodiment.

Similar to FIG. 4 above, the signal responses emitted by the EM sensors at both frequencies in the navigation system 52 are detected and measured. Specifically, the signal response of a first receiving EM sensor (e.g., EM sensor 54) is measured (block 156) at both frequencies. Similarly, the signal response of a second receiving EM sensor (e.g., EM sensor 56) is measured (block 158) at both frequencies. As noted above, because the transmitter is driven at two or more frequencies below approximately 500 Hz, the signal response of both sensors changes due primarily (e.g., only) due to varying distortion.

Specifically, the signal responses of the EM sensors 54 and 56 are generally composed of a real component and an imaginary component. The real component of the signal response represents the sum of the undistorted transmitter response (e.g., undistorted field) and the real part of the distortion response (e.g. distorted field). The imaginary component of the signal response represents the field distortion caused by conductive materials within the field (e.g., distorted field). The signal response is the hypothetical combination of the real component with the imaginary component, and represents the signal as it received by the EM sensors configured to receive the signal response. The signal response, as it is received by the EM sensors may be distorted due to the presence of metallic objects within the field.

In certain embodiments, field distortions are calculated based on characteristic behaviors of distorted fields for irregularly shaped ferromagnetic objects. For example, in distorted fields resulting from irregular ferromagnetic objects, for frequencies lower than 500 Hz, the imaginary components of the response signal can be attributed to distortion and, if calculated, can be discarded to obtain the undistorted field. Furthermore, as described in FIG. 3 above, at frequencies lower than 500 Hz, the field of the transmitter is frequency independent. Given the measured distance between at least two sensors in the navigation system 52, and based on the known correlation between the real component and the imaginary component of irregularly shaped ferromagnetic objects at low frequencies, the field distortion can be calculated (block 160).

In particular, the measured signal response of the receiving sensors of the navigation system 52 (e.g., EM sensors 54 and 56), when distorted by an irregular metallic object for the first frequency at the first sensor, can be described in equation (3) as:

$$M_1 = C_1 + X_1 \quad (3)$$

The measured signal response of the receiving sensors of the navigation system 52 (e.g., EM sensors 54 and 56), when distorted by an irregular metallic object for the first frequency at the second sensor, can be described in equation (4) as:

$$M_2 = C_2 + Y_1 \quad (4)$$

The measured signal response of the receiving sensors of the navigation system 52 (e.g., EM sensors 54 and 56), when distorted by an irregular metallic object for the second frequency at the first sensor, can be described in equation (5) as:

$$M_3 = C_1 + X_2 \quad (5)$$

The measured signal response of the receiving sensors of the navigation system 52 (e.g., EM sensors 54 and 56), when distorted by an irregular metallic object for the second frequency at the second sensor, can be described in equation (6) as:

$$M_4 = C_2 + Y_2 \quad (6)$$

Within these sets of equations, $C_1$ and $C_2$ are the real components of the signal response (e.g., undistorted field emitted by the transmitter) as received by the first and second EM sensor, respectively. Likewise, $X_1$, $X_2$, $Y_1$, and $Y_2$ are the sum of the real and imaginary components of the signal response at each sensor (e.g., distortion caused by conductive materials or distorted field). Thus, given the measured signal responses $M_1$, $M_2$, $M_3$ and $M_4$, and the measured distance between at least two sensors, the imaginary components ($X_1$, $X_2$, $Y_1$, and $Y_2$) and the real components ($C_1$ and $C_2$) can be calculated, and the field distortion can be determined.

As illustrated in FIG. 3, the calculated field distortion for both frequencies obtained at block 160 is used by the position/orientation system 41 to calculate (block 162) the actual field (e.g., undistorted transmitter response). After calculating the distortion, the actual position and orientation coordinates of the device 68 is determined (block 164). In certain embodiments, the position and orientation of the medical device, implant or instrument attached to the sensors of the navigation system 52 may adjusted to compensate for position and orientation errors. In other embodiments, the navigation system 52 may cause the workstation 60 to indicate the correct position and orientation information (e.g., via display 98).

Figure 6:
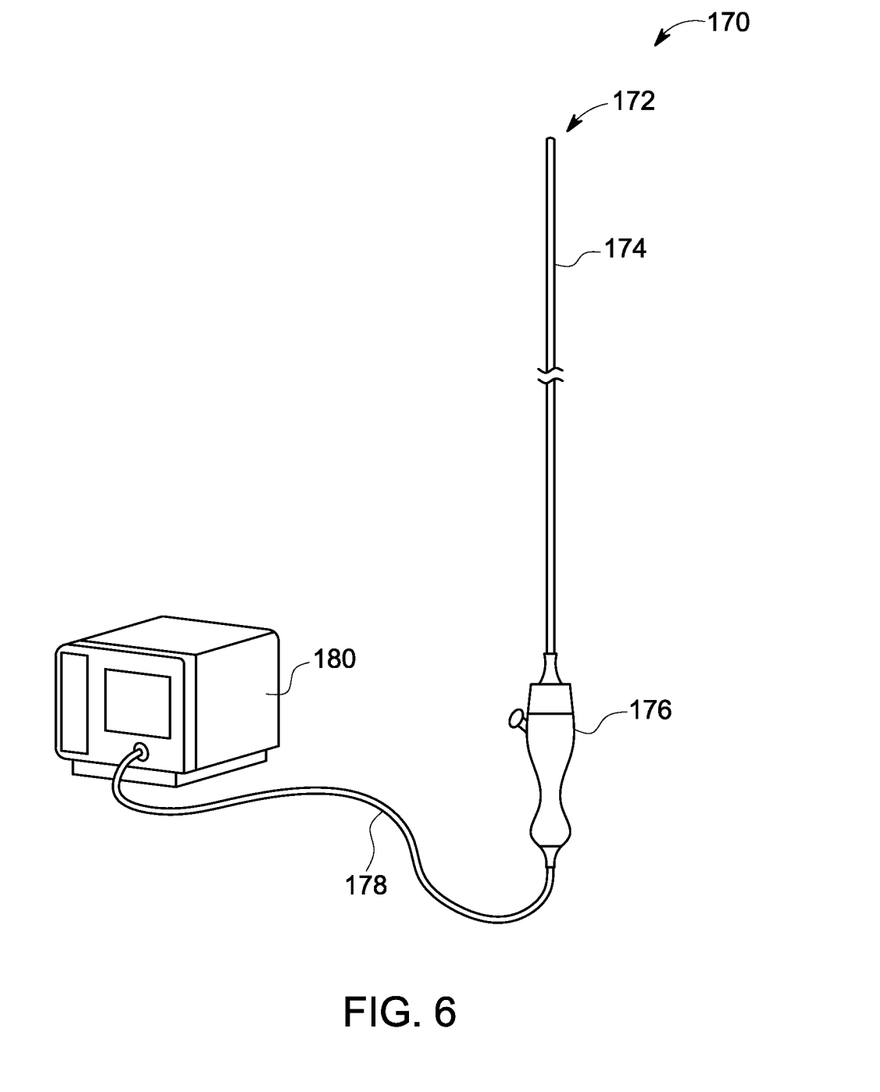
FIG. 6 depicts an example of an interventional device suitable for use with the position and orientation sensor assembly of FIG. 1, in accordance with aspects of the present disclosure.

Turning to FIG. 6, an example of a medical device is depicted that is suitable for use with a position/orientation system 41, and/or the navigation system 52 as discussed herein. In this example, the medical device is a catheter 170 suitable for insertion into and navigation through the vasculature of the patient 18. Though a catheter is provided by way of example, the position/orientation system 41 discussed herein may be provided on or in various other types of surgical or interventional instruments, implants or devices. Examples of such instruments, implants or devices include, but are not limited to: implant, probe, awl, drill, aspirator, forceps, blade, screw, nail, pin, k-wire, needle, cannula, introducer, catheter, guidewire, stent, heart valve, filter, endoscope, laparoscope, or electrode, endoscopes or other intrabody camera devices, or any other suitable device for which position and orientation information may be desired during surgical or interventional use.

Turning back to FIG. 6, the depicted catheter includes a distal end or tip 172 in which the position/orientation system 41 may be positioned as well as a shaft 174 in communication with the tip 172 and which connects the tip 172 with a handle assembly 176 that may be used to manipulate and operate the catheter 170. In certain instances, the handle may communicate, such as via cable 178, with an operator console 180 that allows a user to control certain aspects of the catheter function and operation.

Figure 7:
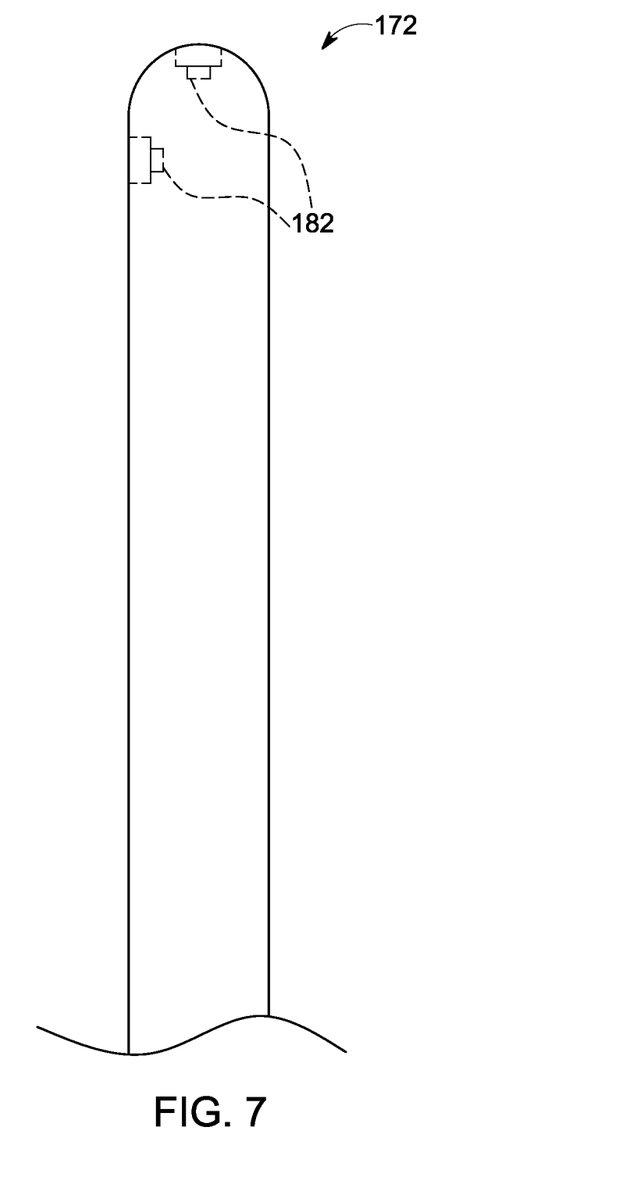
FIG. 7 depicts a distal end or tip of the interventional device of FIG. 6, in accordance with an aspect of the present disclosure.

Turning to FIG. 7, a close-up view of the tip 172 of catheter 170 is provided. In the illustrated embodiment, two position and orientation sensor assemblies 182 are depicted as being positioned within the tip 172. For example, the sensor assemblies may be potted or otherwise affixed into the desired position within the catheter tip 172. While two position and orientation sensor assemblies 182 are shown by way of example, in other embodiments a single sensor assembly 182 may be provided while, in yet other implementations three, four, or more sensor assemblies 182 may be provided in the medical device. Further, to achieve the desired placement and orientation of the sensor assembly 182 in the device (e.g., tip 172), one or both of the sensor assembly 182 and the portion of the device where the sensor assembly 182 is to be placed may be keyed to allow placement on the position and orientation sensor assembly 182 in suitable locations and/or orientations.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
in a medical navigation system:
driving a transmitter at a first frequency and at least a second frequency to generate a first and at least a second electromagnetic field, wherein the first and second frequencies are sufficiently low such that the first and second electromagnetic fields are frequency independent;
receiving a first and at least a second distorted field corresponding to the first and second electromagnetic fields, respectively, with each of at least two electromagnetic (EM) sensors attached to a surgical device;
generating a first and at least a second signal in response to receiving the first and second distorted fields, respectively, using each of the at least two EM sensors; and
determining a distortion in the first and at least the second signals based at least on a distance between the at least two EM sensors and a difference between the first and second signals generated by each of the at least two EM sensors.

2. The method of claim 1, wherein the difference between the first and at least the second signals generated by each of the at least two EM sensors is attributable only to distortion caused by conductive objects disposed proximate the first and second EM sensors.

3. The method of claim 1, comprising correcting the first and at least the second signals for the distortion and determining a position of the surgical device relative to the transmitter based at least on the corrected first and second signals of each of the at least two EM sensors.

4. The method of claim 1, comprising determining a first position of the surgical device relative to the transmitter based on the first and second signals, and then correcting the first and second signals for the distortion and determining a second position of the surgical device relative to the transmitter based at least on the corrected first and second signals of each of the at least two EM sensors.

5. The method of claim 4, comprising displaying, on a display of the medical navigation system, the first position of the surgical device relative to the transmitter on a 2D or 3D representation of at least a patient and the surgical device, and updating the displayed position of the surgical device based on the corrected first and second signals of each of the at least two EM sensors.

6. The method of claim 1, wherein the first and at least the second frequencies are between approximately 500 Hz and 100 Hz.

7. The method of claim 1, wherein the first and at least the second frequencies are below approximately 1 kHz.

8. A medical navigation system, comprising:
a transmitter configured to emit electromagnetic (EM) fields in response to current at one or more frequencies;
first and second EM sensors each configured to detect the EM fields emitted by the transmitter and to generate a signal representative of each detected EM field; and
a computerized navigation system comprising:
one or more tangible, non-transitory, machine-readable media collectively storing instructions executable by a processor to:
drive the transmitter at one or more frequencies to generate one or more EM fields, wherein the one or more frequencies are sufficiently low such that the one or more EM fields are frequency independent;
measure one or more signals generated by the first EM sensor in response to detecting the one or more EM fields, respectively;
measure one or more signals generated by the second EM sensor in response to detecting the one or more EM fields, respectively; and
calculate a distortion in at least one of the one or more signals generated by the first EM sensor and the one or more signals generated by the second EM sensor based at least on a distance between the first and second EM sensors, a change in the one or more signals generated by the first EM sensor and the one or more signals generated by the second EM sensor, and the frequency response of the EM sensors when driven at a frequency of approximately zero.

9. The system of claim 8, further comprising a surgical device, wherein the first and second EM sensors are attached to the surgical device at the distance from one another.

10. The system of claim 9, wherein the instructions are executable by the processor to determine a position and orientation of the surgical device relative to the transmitter based at least on one of the one or more signals generated by the first EM sensor and the one or more signals generated by the second EM sensor and the calculated distortion.

11. The system of claim 10, further comprising a display communicatively coupled to the computerized navigation system, wherein the instructions are executable by the processor to display the position of the surgical device relative to the transmitter on a 2D or 3D representation of at least a patient and the surgical device on the display.

12. The system of claim 11, comprising an X-ray imaging system configured to obtain one or more X-ray images of the patient to produce the 2D or 3D representation of the patient.

13. The system of claim 12, wherein the change in the one or more signals generated by the first EM sensor or the one or more signals generated by the second EM sensor is attributable only to distortion caused by conductive objects disposed proximate the first and second EM sensors, and the conductive objects comprise the surgical device or a portion of the X-ray imaging system.

14. The system of claim 9, wherein the surgical device comprises an implant, probe, awl, drill, aspirator, forceps, blade, screw, nail, pin, k-wire, needle, cannula, introducer, catheter, guidewire, stent, filter, endoscope, laparoscope, electrode, endoscope, or any combination thereof.

15. The system of claim 8, wherein the one or more frequencies are between approximately 500 Hz and 100 Hz.

16. The system of claim 8, wherein the one or more frequencies are below approximately 1 kHz.

17. One or more tangible, non-transitory, machine-readable media collectively storing instructions executable by a processor to:
drive a transmitter at one or more frequencies to generate one or more EM fields, wherein the one or more frequencies are sufficiently low such that the one or more EM fields are frequency independent;
measure one or more signals generated by a first EM sensor in response to detecting the one or more EM fields, respectively;

measure one or more signals generated by a second EM sensor in response to detecting the one or more EM fields, respectively; and calculate a distortion in at least one of the one or more signals generated by the first EM sensor and the one or more signals generated by the second EM sensor based at least on a distance between the first EM sensor and the second EM sensor, a change in the one or more signals generated by the first EM sensor and the one or more signals generated by the second EM sensor, and the frequency response of the first EM sensor and the second EM sensor when driven at a frequency of approximately zero.

18. The media of claim 17, wherein the one or more frequencies are between approximately 500 Hz and 100 Hz.

19. The media of claim 17, wherein the instructions are executable by the processor to determine a position and orientation of a surgical device, to which the first EM sensor and the second EM sensor are attached, relative to the transmitter based at least on at least one of the one or more signals generated by the first EM sensor and the one or more signals generated by the second EM sensor and the calculated distortion.

20. The media of claim 17, wherein the instructions are executable by the processor to cause a position of a surgical device relative to the transmitter to be displayed as a 2D or 3D representation of at least a patient and the surgical device on a display.

* * * * *